United States Patent [19]

Yamaoka et al.

[11] Patent Number: 5,681,685

[45] Date of Patent: Oct. 28, 1997

[54] PHOTOPOLYMERIZABLE COMPOSITION CONTAINING SQUARYLIUM COMPOUND

[75] Inventors: Tsuguo Yamaoka, Funabashi; Kenichi Koseki, Chiba; Ikuo Shimizu, Yokkaichi; Hiroshi Toyoda, Yokkaichi; Hirotaka Kinoshita, Yokkaichi; Shoshiro Matsushita, Yokkaichi, all of Japan

[73] Assignee: Kyowa Hakko Kogyo Co., Ltd., Tokyo, Japan

[21] Appl. No.: 648,136

[22] PCT Filed: Sep. 20, 1995

[86] PCT No.: PCT/JP95/01894

§ 371 Date: May 21, 1996

§ 102(e) Date: May 21, 1996

[87] PCT Pub. No.: WO96/09289

PCT Pub. Date: Mar. 28, 1996

[30] Foreign Application Priority Data

Sep. 21, 1994 [JP] Japan ................. 6-226568

[51] Int. Cl.$^6$ ................. G03F 7/29; G03F 7/28
[52] U.S. Cl. ................. 430/281.1; 522/14; 522/16; 548/427
[58] Field of Search ................. 430/281.1, 944, 430/920; 522/14, 16; 548/427

[56] References Cited

U.S. PATENT DOCUMENTS

| | | | |
|---|---|---|---|
| 4,743,530 | 5/1988 | Farid et al. | 430/281 |
| 4,743,531 | 5/1988 | Farid et al. | 430/281.1 |
| 4,997,745 | 3/1991 | Kawamura et al. | 430/281 |
| 5,147,758 | 9/1992 | Smothers et al. | 430/281.1 |
| 5,275,917 | 1/1994 | Inaishi | 430/288.1 |

FOREIGN PATENT DOCUMENTS

| | | |
|---|---|---|
| 0369645 | 5/1990 | European Pat. Off. |
| 0379200 | 7/1990 | European Pat. Off. |
| 0437259 | 7/1991 | European Pat. Off. |
| 60-224674 | 4/1984 | Japan |
| 63-235370 | 3/1987 | Japan |
| 505005 | 4/1991 | Japan |
| 6263732 | 3/1993 | Japan |

OTHER PUBLICATIONS

World Patent Index Acct. No. C92–1468, Abstract of Japanese Document JP 04106548A Date 920408.

*Primary Examiner*—Cynthia Hamilton
*Attorney, Agent, or Firm*—Fitzpatrick, Cella, Harper & Scinto

[57] ABSTRACT

The present invention relates to a photopolymerizable composition comprising squarylium compound represented by the formula (I):

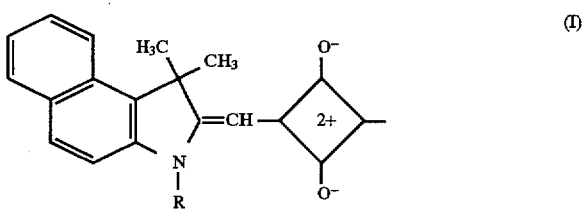
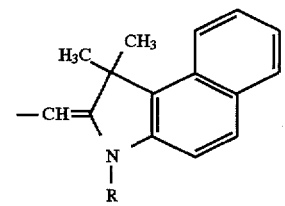

wherein R represents lower alkyl having 2 to 8 carbon atoms, a radical generator and an addition-polymerizable compound having at least one ethylenic unsaturated double bond.

2 Claims, No Drawings

PHOTOPOLYMERIZABLE COMPOSITION CONTAINING SQUARYLIUM COMPOUND

TECHNICAL FIELD

The present invention relates to a photopolymerizable composition containing a squarylium compound. Since the photopolymerizable composition has the high sensitivity to from visible lights having the wavelength of not less than 600 nm near infrared lights, it is useful as a red light sensitive component in visible laser recording materials such as PS plate for laser direct plate making, dry film resist, digital proof, holograph and the like, and panchromatic photosensitive materials such as color hologram photosensitive material, full color designation photosensitive material containing a photopolymerizable composition in a microcapsule, as well as light sensitive materials such as coating agent, adhesive and the like for which visible to near infrared lights sources are used.

BACKGROUND ART

There is disclosed a photopolymerizable composition using a squarylium compound as a sensitizing dye and using a s-triazine compound as a radical generator in JP-A 2-48665, JP-A 2-229802, JP-A 2-306247, JP-A 4-106548, JP-A 5-5005 and the like.

There are known a photopolymerizable composition using a squarylium compound as a sensitizing dye and an azinium salt as a radical generator (for example, JP-A 63-142346), a photopolymerizable composition using hexaarylbisimidazole (for example, JP-A 5-27436), a photopolymerizable composition using a metal-allene complex (for example, JP-A 5-17525) and the like, respectively.

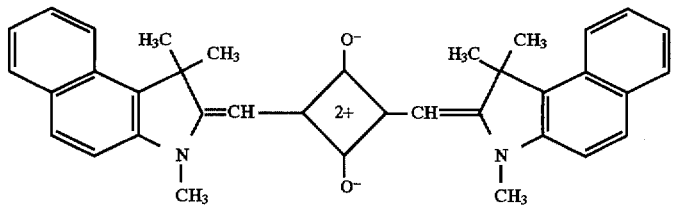

(A)

It is disclosed in JP-A 63-138345, JP-A 63-142346, JP-A 2-48665 and the like that a benzoindolenium salt compound represented by the above formula (A) has the maximum absorption wavelength at 673 nm. The benzoindolenium salt compound has a problem that, although it can effectively sensitize various red lasers, for example, He—Ne laser, Kr laser, short wavelength semiconductor laser due to the above property, since it has the low solubility in an organic solvent or a monomer, the higher concentration in a photosensitizer solution can not be obtained and, therefore, the use of solvents having the low toxicity, for example, methyl ethyl ketone is limited. In addition, the benzoindolenium salt compound has also a problem that, since it is easily degraded in the dark even when stored with the light screened in a photosensitizer solution, the photosensitizer solution is discolored in a red region and the photosensitivity of the solution to the red light is remarkably lowered in a short period of time.

DISCLOSURE OF THE INVENTION

The present invention relates to a photopolymerizable composition which comprises a squarylium compound represented by the formula (I):

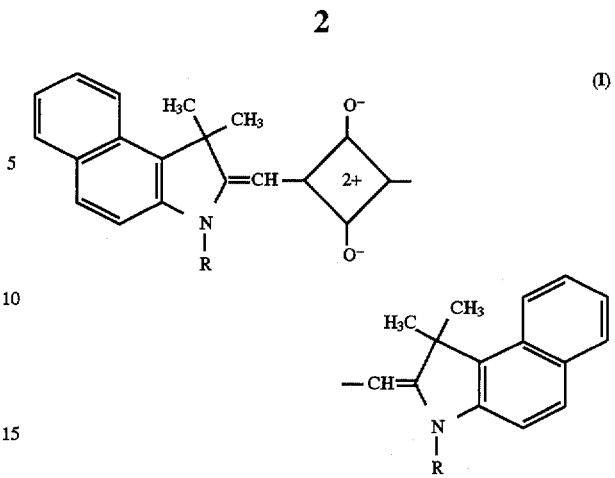

wherein R represents lower alkyl having 2 to 8 carbon atoms, a radical generator and an addition-polymerizable compound having at least one ethylenic unsaturated double bond.

According to the present invention, there is also provided a squarylium compound represented by the formula (Ia):

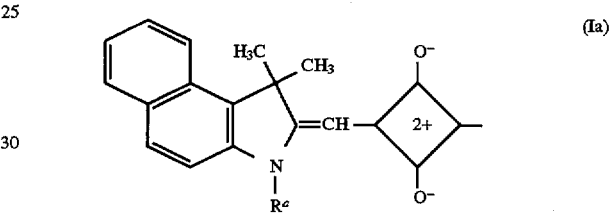

-continued

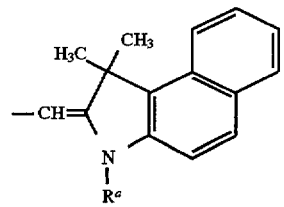

wherein $R^a$ represents propyl, isopropyl, isobutyl, pentyl, isopentyl or hexyl.

Hereinafter, compounds represented by the formula (I) and (Ia) are referred to as "Compound (I)" and "Compound (Ia)", respectively. The same applies to the compounds of other formula numbers.

In the definition of the formula (I), examples of lower alkyl having 2 to 8 carbon atoms are straight or branched alkyls such as ethyl, propyl, isopropyl, butyl, isobutyl, sec-butyl, tert-butyl, 2-ethylbutyl, pentyl, isopentyl, neopentyl, 3-ethylpentyl, tert-pentyl, hexyl, isohexyl, heptyl, octyl and the like.

Then, a process for preparation of Compound (I) is described below:

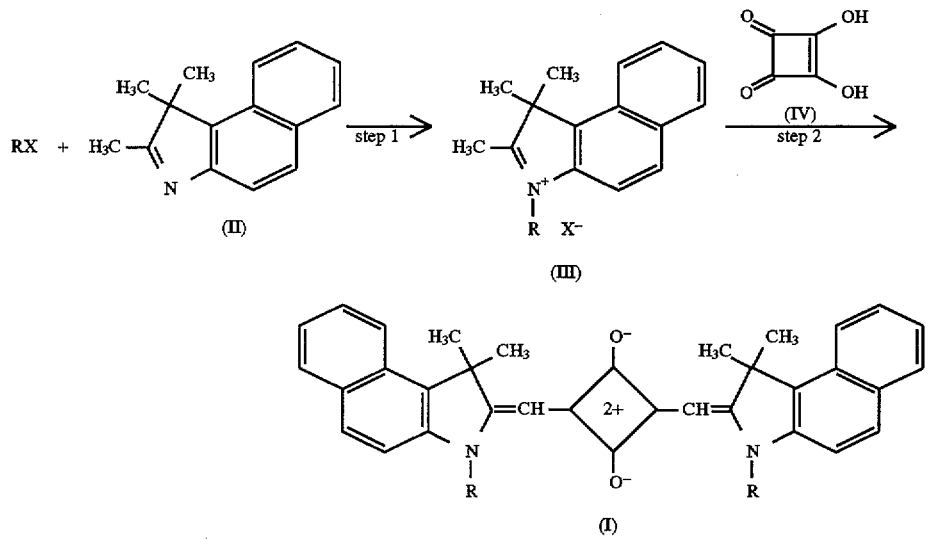

(In the formula, R has the same meaning as defined above, and X represents halogen or p-toluenesulfonyloxy.)

As used herein, halogen represents chlorine, bromine or iodine.

A raw compound (II) can be obtained according to a process described in Monatsh. Chem., 31, 123 (1910) or a similar process thereto.

Step 1

Compound (III) can be prepared by reacting Compound (II) with an equivalent to a large excess amount of compound RX in a solvent or without a solvent under heating for 1 to 24 hours. Examples of the solvent to be used are methyl isobutyl ketone, diisobutyl ketone, xylene, toluene, butanol and the like.

Step 2

Compound (I) can be obtained by reacting Compound (III) with 0.5 equivalent of Compound (IV) at 90 to 110° C. for 1 to 24 hours in a solvent in the presence of 1 to 2 equivalents of a basic compound. Examples of the basic compound are triethylamine, quinoline, pyridine and the like. Examples of the solvent are alcohols such as ethanol, butanol, isobutylalcohol, pentanol, hexanol, heptanol, octanol and the like, and a mixed solvent of the above alcohol and an aromatic hydrocarbon such as benzene, toluene, xylene or the like.

Intermediates and the desired compounds in the above process can be isolated and purified by the purification method, conventionally used in organic synthetic chemistry, such as filtration, extraction, washing, drying, concentration, crystallization, and various kinds of chromatography. Alternatively, intermediates can be used in the next reaction without purification.

Compound (I) may be obtained as crystals comprising Compound (I) and an organic solvent such as benzene, toluene, xylene, alcohol or the like and these crystals may be used as the present squarylium compound.

Embodiments of Compound (I) are listed in Table 1.

TABLE 1

| Compound | R |
|---|---|
| 1 | —$CH_2CH_3$ |
| 2 | —$(CH_2)_2CH_3$ |
| 3 | —$CH(CH_3)_2$ |
| 4 | —$(CH_2)_3CH_3$ |
| 5 | —$CH_2CH(CH_3)CH_3$ |
| 6 | —$(CH_2)_4CH_3$ |
| 7 | Crystals comprising of Compound 4 and o-xylene (1:1 molar ratio) |
| 8 | Crystals comprising of Compound wherein R is —$(CH_2)_2CH(CH_3)CH_3$ and o-xylene (1:1 molar ratio) |
| 9 | —$(CH_2)_5CH_3$ |

Then, the photopolymerizable composition of the present invention is explained below.

The photopolymerizable composition can be prepared by mixing Compound (I), a radical generator and an addition-polymerizable compound (hereinafter, also referred to as "ethylenic compound") having at least one ethylenic unsaturated double bond and, if necessary, a binder and the conventional additive (such as thermal polymerization-inhibitor, plasticizer and the like).

Examples of the radical generator are s-triazine compounds substituted with at least one trihalomethyl group (such as 2,4,6-tris(trichloromethyl)-s-triazine, 2-(4-methoxyphenyl)-4,6-bis(trichloromethyl)-s-triazine, 2-(4-methoxy-1-naphthyl)-4,6-bis(trichloromethyl)-s-triazine and the like); organic peroxide compounds (such as 3,3',4,4'-tetrakis(tert-butyldioxycarbonyl)benzophenone and the like); N-phenylglycines (such as N-phenylglycine, p-chloro-N-phenylglycine, m-methyl-N-phenylglycine and the like); aromatic sulfonyl halide compounds (such as benzenesulfonyl chloride, p-toluenesulfonyl chloride and the like); imidazole dimers [such as 2,2'-bis(o-chlorophenyl)-4,4',5,5'-tetraphenylbiimidazole and the like], metal-allene complexes [such as ($\eta^6$-benzene)($\eta^5$-cyclopentadienyl)iron (II) hexafluorophosphate, fluoroaryl titanocene and the like]; diaryliodonium salt (such as 8-anilinonaphthalene-1-sulfonic acid diphenyliodonium salt and the like); triaryl sulfonium salt; branched polyethyleneimines; alkyl or aryl borate (such as tetrabutylammonium triphenylbutyl borate and the like); aromatic ketones (such as thioxanthon and the like); acetophenones (such as benzoinether, benzyl dimethyl ketal and the like); diketones; acyl oxime esters; sulfur compounds (such as thiol, disulfide and the like). The present photopolymerization initiator system is composed of a squarylium compound and a radical generator. An amount of the radical generator to be used in the photopolymerization initiator is 0.1 to 100 parts by weight (hereinafter, part(s) by weight is referred to as "part(s)"), preferably 1 to 50 parts relative to 1 part of the squarylium compound.

Examples of the ethylenic compound may be any compounds which have at least one ethylenic unsaturated double bond, which addition-polymerize by means of radicals produced when the photopolymerizable composition is exposed to the light, and which cause hardening and insolubilization of the photopolymerizable composition. For example, monomers and oligomers having at least one ethylenic unsaturated double bond and polymers having at least one ethylenic unsaturated double bond in a main or side chain are used alone or in combination.

Examples of the monomer having at least one ethylenic unsaturated double bond are unsaturated carboxylic acids, esters of an unsaturated carboxylic acid and monohydroxy compound, esters of an unsaturated carboxylic acid and aliphatic polyhydroxy compound, esters of an unsaturated carboxylic acid and aromatic polyhydroxy compound, and esters obtained by esterification of an unsaturated carboxylic acid, polyvalent carboxylic acid and polyhydroxy compound.

Examples of the unsaturated carboxylic acid are acrylic acid, methacrylic acid, itaconic acid, crotonic acid, maleic acid and the like.

Examples of the ester of the unsaturated carboxylic acid and the monohydroxy compound are acrylates such as methyl acrylate, butyl acrylate, 2-phenoxyethyl acrylate, p-chlorophenyl acrylate, 2-(1-naphthyloxy)ethyl acrylate, o-biphenyl acrylate, pentachlorophenyl acrylate, 2,4,6-tribromophenyl acrylate, 2-naphthyl acrylate, 2-(2-naphthyloxy)ethyl acrylate, trifluoroethyl acrylate, tetrafluoropropyl acrylate, dibromopropyl acrylate, ethyl-2-chloro acrylate, tetrahydrofurfuryl acrylate and the like, and compounds wherein an acrylic acid part is replaced by methacrylic acid in the above acrylates, as well as derivatives thereof.

Examples of the ester of the unsaturated carboxylic acid and the aliphatic polyhydroxy compound are acrylates such as ethylene glycol diacrylate, triethylene glycol diacrylate, tetraethylene glycol diacrylate, propylene glycol diacrylate, neopentyl glycol diacrylate, 1,3-butanediol diacrylate, 1,4-cyclohexanediol diacrylate, hexanediol diacrylate, trimethylolpropane triacrylate, trimethylolethane triacrylate, trimethylolpropane tris(acryloyloxypropyl) ether, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, glycerol acrylate, sorbitol triacrylate, sorbitol tetraacrylate, sorbitol pentaacrylate, sorbitol hexaacrylate and the like, and compounds wherein an acrylic acid part is replaced by methacrylic acid in the acrylates, as well as itaconates, crotonates and maleates of the aliphatic polyhydroxy compound.

Examples of the ester of the unsaturated carboxylic acid and the aromatic polyhydroxy compound are hydroquinone diacrylate, hydroquinone dimethacrylate, resorcin diacrylate, resorcin dimethacrylate and pyrogallol triacrylate, as well as esters of an unsaturated carboxylic acid and aromatic polyhydroxy compound derivative such as EO-modified bisphenol A diacrylate, tris(β-acryloyloxyethyl)-s-cyanurate and the like.

Examples of the ester obtained by esterification of the unsaturated carboxylic acid, polyvalent carboxylic acid and polyhydroxy compound are a condensation product from acrylic acid, phthalic acid and ethylene glycol, a condensation product from acrylic acid, maleic acid and diethylene glycol, a condensation product from methacrylic acid, terephthalic acid and pentaerythritol, a condensation product from acrylic acid, adipic acid, butanediol and glycerin, a condensation product from acrylic acid, trimellitic acid and diethylene glycol and the like.

The other examples of the monomer or oligomer having at least one ethylenic unsaturated double bond used in the present invention are acrylic amides such as ethylenebisacrylamide and the like, allyl esters such as diacryl phthalate and prepolymer thereof, vinyl group-containing compounds such as divinyl phthalate and the like, urethane acrylate such as a condensation product from glycerin dimethacrylate and hexamethylene diisocyanate and the like, N-vinylcarbazole, N-vinylpyrrolidone and the like.

Examples of the polymer having an ethylenic unsaturated double bond on a main chain are polyesters obtained by polycondensation of an unsaturated divalent carboxylic acid and dihydroxy compound, polyamides obtained by polycondensation of an unsaturated divalent carboxylic acid and diamine and the like.

Examples of the polymer having an ethylenic unsaturated double bond on a side chain are polycondensation products from a divalent carboxylic acid having an unsaturated bond on a side chain such as itaconic acid, propylidenesuccinic acid, ethylidenemalonic acid and the like, and dihydroxy or diamine compound. Alternatively, polymers having a functional group such as a hydroxy group, halogenated methyl group, epoxy group or the like on a side chain may be used, such as a polymer obtained by polymeric reaction of polyvinyl alcohol, poly(2-hydroxyethyl methacrylate), epoxy resin, phenoxy resin polyepichlorohydrine or the like, with an unsaturated carboxylic acid such as acrylic acid, methacrylic acid, crotonic acid or the like.

Examples of the binder are a polymethacrylate or partial hydrolysate thereof, a polyacrylate or partial hydrolysate thereof, polyvinyl acetate or a partial hydrolysate thereof, a vinyl acetate-ethylene copolymer or partial hydrolysate thereof, polystyrene, polyvinyl formal, polyvinylbutyral, polychloroprene, polyvinyl chloride, chlorinated polyethylene, chlorinated polypropylene, phenol novolak or cresol novolak resin, polyvinyl phenol, vinyl phenol-methacrylate copolymer, polyethylene oxide, polymethyl isopropenyl ketone, methacrylate-phenyl isopropenyl ketone copolymer, polyurethane, polyamide, polycarbonate, polyethylene terephthalate, polybutylene terephthalate, acetylcellulose, acetylbutylcellulose, nitrocellulose, polyvinyl carbazole or a derivative thereof, a vinylcarbazole-styrene copolymer, a vinylcarbazole-methacrylate copolymer, a vinylcarbazole-acrylate copolymer, polyvinyl pyrrolidone or a derivative thereof, a vinylpyrrolidone-styrene copolymer, a vinylpyrrolidone-methacrylate copolymer, a vinylpyrrolidone-acrylate copolymer, and a styrene-maleic acid (monoester) copolymer, as well as a copolymer obtained from at least two members selected from copolymerizable monomers such as acrylates, acrylic acid, methacrylates, methacrylic acid, maleic acid (anhydride), acrylonitrile, acrylamide, styrene, vinyl acetate, vinyl chloride, vinylidene chloride, butadiene, isoprene, chloroprene and the like.

Examples of the thermal polymerization-inhibitor are p-tert-butylcatechol, hydroquinone, chloranyl and the like.

Examples of the plasticizer are diethylhexyl phthalate, diisobutyl phthalate, tricresyl phosphate, diethylhexyl cebacate, diethylhexyl adipate and the like.

An amount of the squarylium compound and that of the radical generator to be used in the photopolymerizable composition are 0.1 to 30 parts, preferably 0.5 to 5 parts, and 1 to 50 parts, preferably 2 to 30 parts relative to 100 parts of the ethylenic compound, respectively.

An amount of the binder to be used is 10 to 1000 parts, preferably 60 to 200 parts relative to 100 parts of the ethylenic compound.

Then, the solubility, of the squarylium compound used in the present invention, in an organic solvent is shown by Test Examples.

TEST EXAMPLE 1

5 ml of ethyl cellosolve and a squarylium compound were added to a 20 ml glass container to an extent that some of the squarylium compound remained unsolved. After squarylium compound crystals were made fine with an ultrasonic cleaning machine for 10 minutes and the mixture was stirred with a stirrer for 20 hours. After the unsolved squarylium compound crystals were removed by filtration and the filtrate was diluted x-folds with chloroform, the absorbance at the maximum absorption wavelength present in 600 to 700 nm was measured with a spectrophotometer. The solubility of the squarylium compound in ethyl cellosolve was obtained according to the following equation:

Solubility (mg/ml)=$x \cdot A \cdot Mw/\epsilon$

X; Degree of dilution
A; Absorbance at maximum absorption wavelength ($cm^{-1}$)
Mw; Molecular weight of squarylium compound (g/mol)
$\epsilon$; Molar extinction coefficient at maximum absorption wavelength (1/mol·cm)

The solubilities of Compounds 1 to 9 are shown as a relative value based on the standard of the solubility of Compound (A) in Table 2.

TABLE 2

| Compound | Relative value of solubility |
|---|---|
| 1 | 37 |
| 2 | 12 |
| 3 | 14 |
| 4 | 95 |
| 5 | 4.4 |
| 6 | 30 |
| 7 | 111 |
| 8 | 38 |
| 9 | 6.8 |
| A | 1.0 |

TEST EXAMPLE 2

The solubility of the squarylium compound in chlorobenzene was obtained according to the same procedures as those in Test Example 1 except for using chlorobenzene in place of ethyl cellosolve. The solubilities of Compounds 1 to 9 are shown as a relative value based on the solubility of Compound (A) in Table 3.

TABLE 3

| Compound | Relative value of solubility |
|---|---|
| 1 | 1.1 |
| 2 | 8.7 |
| 3 | 1.8 |
| 4 | 24 |
| 5 | 4.1 |
| 6 | 51 |
| 7 | 27 |
| 8 | 30 |
| 9 | 31 |
| A | 1.0 |

TEST EXAMPLE 3

The solubility of the squarylium compound in methyl ethyl ketone was obtained according to the same procedures as those in Test Example 1 except for using methyl ethyl ketone in place of ethyl cellosolve. The solubilities of Compounds 1 to 9 are shown as a relative value based on the standard of the solubility of Compound (A) in Table 4.

TABLE 4

| Compound | Relative value of solubility |
|---|---|
| 1 | 6.8 |
| 2 | 3.5 |
| 3 | 4.4 |
| 4 | 103 |
| 5 | 1.8 |
| 6 | 11 |
| 7 | 131 |
| 8 | 42 |
| 9 | 4.7 |
| A | 1.0 |

The embodiments of the present invention are shown by Examples below.

Compound 1 is a known compound described in JP-A 3-126581 and Compound 4 is a known compound described in JP-A 1-178493 and they can be obtained according to a method described in U.S. Pat. No. 4,830,786.

BEST MODE FOR CARRYING OUT THE INVENTION

EXAMPLE 1

A mixture of 0.80 g of 3,4-dihydroxy-3-cyclobutene-1,2-dione, 5.99 g of 2,3,3-trimethyl1-propyl-3H-benzoindolium p-toluenesulfonate obtained in Reference Example 1, 1.64 g of quinoline, 30 ml of butanol and 30 ml of benzene was stirred under reflux for 11 hours. After the reaction solution was concentrated, 30 ml of ethanol was added to the residue, followed by heating for 30 minutes. After cooling, the crystals were filtered off and dried in vacuo to give 2.07 g of Compound 2.

Melting point: not lower than 280° C.

Elemental analysis

Calc'd (%): C 82.71, H 6.96, N 4.82

Found (%): C 82.25, H 6.85, N 4.53

Optical absorption property:

| Solvent | Chloroform |
|---|---|
| $\lambda_{max}$ | 667 nm |
| $\log \epsilon$ | 5.5 |

EXAMPLE 2

A mixture of 0.80 g of 3,4-dihydroxy-3-cyclobutene-1,2-dione, 5.99 g of 1-isopropyl-2,3,3-trimethyl-3H-benzo[e]-indolium p-toluenesulfonate, 1.64 g of quinoline, 30 ml of butanol and 30 ml of benzene was stirred under reflux for 11 hours. After the reaction solution was concentrated, the residue was purified by column chromatography to give 0.80 g of Compound 3.

Melting point: not lower than 280° C.

Elemental analysis:

Calc'd (%): C 82.71, H 6.96, N 4.82

Found (%): C 81.94, H 6.99, N 4.62

Optical absorption property:

| Solvent | Chloroform |
|---|---|
| $\lambda_{max}$ | 666 nm |
| $\log \epsilon$ | 5.5 |

EXAMPLE 3

A mixture of 0.57 g of 3,4-dihydroxy-3-cyclobutene-1,2-dione, 4.42 g of 1-isobutyl-2,3,3-trimethyl-3H-benzo[e]-indolium p-toluenesulfonate, 1.64 g of quinoline, 30 ml of butanol and 30 ml of benzene was stirred under reflux for 7 hours. After the reaction solution was concentrated, the residue was purified by column chromatography to give 0.96 g of Compound 5.

Melting point: not lower than 280° C.

Elemental analysis:

Calc'd (%): C 82.84, H 7.30, N 4.60

Found (%): C 81.21, H 7.30, N 4.51

Optical absorption property:

| Solvent | Chloroform |
|---|---|
| $\lambda_{max}$ | 669 nm |
| $\log \epsilon$ | 5.5 |

EXAMPLE 4

A mixture of 0.80 g of 3,4-dihydroxy-3-cyclobutene-1,2-dione, 6.40 g of 2,3,3-trimethyl-1-pentyl-3H-benzo[e]-indolium p-toluenesulfonate, 1.17 g of quinoline, 25 ml of butanol and 25 ml of benzene was stirred under reflux for 11 hours. After the reaction solution was concentrated, the residue was purified by column chromatography to give 2.70 g of Compound 6.

Melting point: not lower than 280° C.

Elemental analysis:

Calc'd (%): C 82.98, H 7.60, N 4.40

Found (%) : C 82.62, H 7.65, N 4.38

Optical absorption property:

| Solvent | Chloroform |
|---|---|
| $\lambda_{max}$ | 667 nm |
| $\log \epsilon$ | 5.5 |

EXAMPLE 5

A mixture of 1.14 g of 3,4-dihydroxy-3-cyclobutene-1,2-dione, 9.03 g of 1-isopentyl-2,3,3-trimethyl-3H-benzo[e]-indolium p-toluenesulfonate, 3.10 g of quinoline, 15 ml of butanol and 30 ml of o-xylene was stirred under reflux for 3 hours. After the reaction solution was concentrated, the precipitated solid was filtered off and dried in vacuo to give 4.69 g of Compound 8.

Melting point: not lower than 280° C.

Elemental analysis:

Calc'd (%): C 84.06, H 7.87, N 3.77

Found (%): C 83.83, H 8.02, N 3.63

Optical absorption property:

| Solvent | Chloroform |
|---|---|
| $\lambda_{max}$ | 667 nm |
| $\log \epsilon$ | 5.5 |

EXAMPLE 6

A mixture of 1.14 g of 3,4-dihydroxy-3-cyclobutene-1,2-dione, 9.31 g of 1-hexyl-2,3,3-trimethyl-3H-benzo[e]-indolium p-toluenesulfonate, 3.10 g of quinoline, 15 ml of butanol and 30 ml of o-xylene was stirred under reflux for 3 hours. After the reaction solution was concentrated, 15 ml of ethanol was added to the residue, followed by heating for 30 minutes. The precipitated crystals were filtered off and dried in vacuo to give 4.29 g of Compound 9.

Melting point: not lower than 280° C.

Elemental analysis:

Calc'd (%): C 83.09, H 7.88, N 4.17

Found (%): C 83.09, H 8.31, N 3.93

Optical absorption property:

| Solvent | Chloroform |
|---|---|
| $\lambda_{max}$ | 668 nm |
| $\log \varepsilon$ | 5.5 |

EXAMPLE 7

0.5 g of pentaerythritol triacrylate, 0.5 g of butyl methacrylate/acrylic acid copolymer (weight-average molecular weight 3,100, copolymerization ratio 66/34), 60 mg of 2,4,6-tris(trichloromethyl)-s-triazine and 2 mg of a squarylium compound were dissolved in ethyl cellosolve to 25 ml to give a photosensitive resin solution. This solution was light-screened and allowed to stand at 40° C. for 3 days. The absorbance at the maximum absorption wavelength present in 600 to 700 nm was measured with a spectrophotometer before (A1) and after (A2) being allowed to stand. The degraded rate of the squarylium compound was obtained according to the following equation:

Degraded rate (%)=(A1−A2)/A1 ×100

The degraded rates of squarylium Compounds 1 to 9 are shown as a relative value based on the degraded rate of Compound (A) in Table 5.

TABLE 5

| Compound | Relative value of degraded rate |
|---|---|
| 1 | 0.34 |
| 2 | 0.25 |
| 3 | 0.24 |
| 4 | 0.29 |
| 5 | 0.15 |
| 6 | 0.28 |
| 7 | 0.31 |
| 8 | 0.32 |
| 9 | 0.26 |
| A | 1.0 |

EXAMPLE 8

0.5 g of pentaerythritol triacrylate, 60 mg of polymethyl methacrylate (manufactured by Aldrich; weight-average molecular weight 12,000), 90 mg of ($\eta^6$-benzene)($\eta^5$cyclopentadienyl)iron(II) hexafluorophosphate and 2 mg of a squarylium compound were dissolved in ethyl cellosolve to 25 ml to give a photosensitive resin solution. Thereafter, the same procedures as those in Example 7 were repeated except that a time for being allowed to stand of 3 days was replaced with that of 32 days to give the degraded rate of the squarylium compound. The degraded rate of squarylium Compounds 1 to 9 are shown as a relative value based on the degraded rate of Compound (A) in Table 6.

TABLE 6

| Compound | Relative value of degraded rate |
|---|---|
| 1 | 0.51 |
| 2 | 0.48 |
| 3 | 0.44 |
| 4 | 0.60 |
| 5 | 0.42 |
| 6 | 0.46 |
| 7 | 0.56 |
| 8 | 0.43 |
| 9 | 0.52 |
| A | 1.0 |

EXAMPLE 9

100 parts of pentaerythritol triacrylate, 100 parts of polymethacrylate polymer [synthesized according to the methods described in Jikkenkagakukoza, Maruzen K. K., 4th edition, volume 28, page 121, 1992; Kobunshigosei no Jikkenho (Experimental method for polymer synthesis), Kagakudojin K. K., coauthored by Takayuki Otsu and Masaetsu Kinoshita, page 138, 1972; average molecular weight 150,000; methyl ester/isobutyl ester/cyclohexyl ester/free carboxylic acid=27/36/25/12], 7.9 parts of 2,4,6-tris(trichloromethyl)-s-triazine and 1 part of a squarylium compound were dissolved in 1900 parts of ethyl cellosolve to give a photosensitive resin solution. This photosensitive solution was spin-coated on an aluminium plate treated with grinding and anodic oxidation, at 1000 rpm so that the dry-state thickness became 2 μm. On this, a 10% aqueous polyvinyl alcohol (Kurarey Poval 706) solution was spin-coated at 1500 rpm so that the dry-state thickness became 1 μm to give a over-coat layer. A step tablet was piled closely on the resulting photosensitive layer, and the rays having the wavelength around 630, 650 or 680 nm were irradiated from 3kw ultra-high pressure mercury lamp through a glass filter. The rays having the wavelength around 630 nm (155 μJ/cm²·s) were obtained by passing the rays from the above mercury lamp through a colored glass filter R-61, an interference filter KL-63 (both were manufactured by Toshiba Glass Co., Ltd.) and a heat rays absorbing filter HA-30 (manufactured by HOYA Corporation), the rays having the wavelength around 650 nm (177 μJ/cm²·s) were obtained by passing the rays from the above mercury lamp through a colored glass filter R-63, an interference filter KL-65 (both were manufactured by Toshiba Glass Co., Ltd.) and HA-30 and the rays having the wavelength around 680 nm (88 μJ/cm²·s) were obtained by passing the rays from the above mercury lamp through a glass filter R-66, an interference filter KL-68 (both were manufactured by Toshiba Glass Co., Ltd.) and HA-30. Then, the development was carried out with a PS plate developer DN3C (manufactured by Fujiphoto Film Co., Ltd.) diluted 1.5-folds with distilled water, an ink was attached thereon with a PS plate developing ink PI-2 (manufactured by Fujiphoto Film Co., Ltd.) and the sensitivity was scored by obtaining an energy amount necessary for hardening from hardening step number with an ink attached thereto. The results are shown in Table 7.

TABLE 7

| Compound | Sensitivity (mJ/cm²) | | |
|---|---|---|---|
| | 630 nm | 650 nm | 680 nm |
| 1 | 0.47 | 0.40 | 0.37 |
| 2 | 0.47 | 0.40 | 0.37 |
| 3 | 0.39 | 0.40 | 0.26 |
| 4 | 0.39 | 0.40 | 0.37 |
| 5 | 0.47 | 0.56 | 0.28 |
| 6 | 0.56 | 0.40 | 0.37 |
| 7 | 0.47 | 0.40 | 0.37 |
| A | 0.91 | 0.56 | 0.65 |

EXAMPLE 10

The sensitivity when the rays having the wavelength around 630 nm were irradiated was obtained by repeating the same procedures as those in Example 9 except that 8 parts of (η⁶-benzene) (η⁵-cyclopentadienyl)iron(II) hexafluorophosphate was used in place of 7.9 parts of 2,4,6-tris(trichloromethyl)-s-triazine and CARBOSET,XL-44 (manufactured by BF Goodrich) was used in place of polymethacrylate polymer (methyl ester/isobutyl ester/cyclohexyl ester/free carboxylic acid=27/36/25/12). The results are shown in Table 8.

TABLE 8

| Compound | Sensitivity (mJ/cm²) |
|---|---|
| 5 | 11 |
| 6 | 5.8 |
| 7 | 5.8 |
| 9 | 8.7 |
| A | 11 |

EXAMPLE 11

The sensitivity when the rays having the wavelength around 630 nm were irradiated was obtained by repeating the same procedures as those of Example 9 except that 8 parts of 3,3',4,4'-tetrakis(tert-butyldioxycarbonyl) benzophenone was used in place of 7.9 parts of 2,4,6-tris (tichloromethyl)-s-triazine. The results are shown in Table 9.

TABLE 9

| Compound | Sensitivity (mJ/cm²) |
|---|---|
| 3 | 0.083 |
| 5 | 0.20 |
| 6 | 0.099 |
| 7 | 0.20 |
| 9 | 0.17 |
| A | 0.43 |

REFERENCE EXAMPLE 1

A mixture of 5.23 g of 2,3,3-trimethyl-3H-benzo[e]-indole and 5.36 g of propyl p-toluenesulfonate was heated at 150° C. for 2 hours. After cooling, the solid in the container was washed with diethyl ether and dried in vacuo to give 9.64 g of a crude product of 2,3,3-trimethyl-1-propyl-3H-benzo[e]indolium p-toluenesulfonate.

INDUSTRIAL APPLICABILITY

According to the present invention, there can be provided a photopolymerizable composition, which contains a squarylium compound which is excellent in the solubility in an organic solvent and is stably present in a photosensitizer solution, which has the high sensitivity to visible lights having the wavelength of not lower than 600 nm to near infrared lights and which is stable upon storage.

We claim:

1. A photopolymerizable composition comprising a squarylium compound represented by the formula (I):

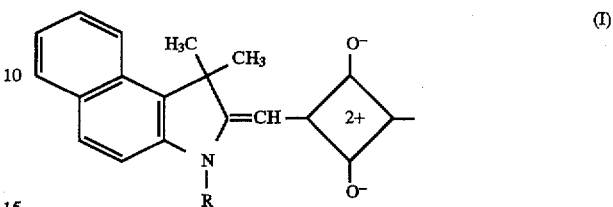

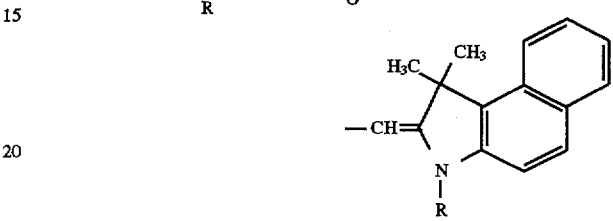

wherein R represents lower alkyl having 2 to 8 carbon atoms, a radical generator and an addition-polymerizable compound having at least one ethylenic unsaturated double bond.

2. A squarylium compound represented by the formula (Ia):

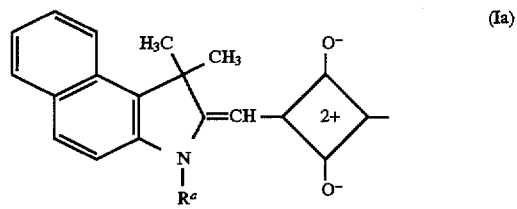

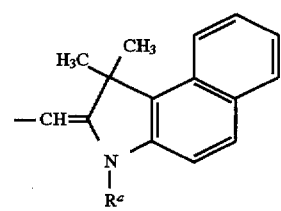

wherein Rᵃ represents propyl, isopropyl, isobutyl, pentyl, isopentyl or hexyl.

* * * * *

UNITED STATES PATENT AND TRADEMARK OFFICE
CERTIFICATE OF CORRECTION

PATENT NO. : 5,681,685

DATED : October 28, 1997

INVENTOR(S): TSUGUO YAMAOKA ET AL.

It is certified that error appears in the above-identified patent and that said Letters Patent is hereby corrected as shown below:

ON TITLE PAGE AT [57], ABSTRACT
  "comprising squarylium" should read --comprising a squarylium--.

COLUMN 1
  Line 8, "from visible lights having the wavelength of" should read --light having the wavelength from--.
  Line 9, "near" should read --to near--.

COLUMN 9
  Line 7, "benzoindolium" should read --benzo[e]indolium--.

COLUMN 12
  Line 25, "give a over-coat" should read --give an over-coat--.

Signed and Sealed this

Twenty-eighth Day of April, 1998

Attest:

BRUCE LEHMAN

*Attesting Officer*   Commissioner of Patents and Trademarks